United States Patent [19]
Larsson et al.

[11] Patent Number: 5,500,413
[45] Date of Patent: Mar. 19, 1996

[54] PROCESS FOR MANUFACTURE OF 1-DEAMINO-8-D-ARGININE VASOPRESSIN

[75] Inventors: Krister Larsson; Thomas Mellbrand; Birgitta Mörnstam, all of Malmö; Jan Roschester, Lund; Jan-Åke Sköldbäck, Malmö, all of Sweden

[73] Assignee: Ferring AB, Malmo, Sweden

[21] Appl. No.: 84,847

[22] Filed: Jun. 29, 1993

[51] Int. Cl.$^6$ ............... A61K 38/00; C07K 5/00; C07K 7/00; C07K 17/00
[52] U.S. Cl. ............... 514/15; 530/315; 530/328
[58] Field of Search ............... 530/315, 328; 514/15

[56] References Cited

U.S. PATENT DOCUMENTS

| | | |
|---|---|---|
| 3,497,491 | 2/1970 | Zaoral et al. |
| 3,794,633 | 2/1974 | Kamber et al. |
| 3,929,758 | 12/1975 | Hughes et al. |
| 4,033,940 | 7/1977 | Hughes et al. |
| 4,093,610 | 6/1978 | Abraham et al. |
| 4,216,141 | 8/1980 | Rivier et al. |
| 4,271,068 | 6/1981 | Kamber et al. |
| 4,351,764 | 9/1982 | Birr. |
| 4,487,765 | 12/1984 | de Wied ............... 424/177 |
| 5,066,716 | 11/1991 | Robey et al. ............... 525/54.1 |

FOREIGN PATENT DOCUMENTS

| | | |
|---|---|---|
| 7308638 | 1/1974 | Netherlands. |

OTHER PUBLICATIONS

Zaoral et al, Coll. Czech. Chem. Comm. vol. 32 pp. 1250–1257 (1967).
Jones et al J. Org. Chem. vol. 38 pp. 2865–2869 (1973).
Article entitled "Titanium (III) as a Selective Reducing Agent for Nitroarginyl Peptides: Synthesis of Arginine Vasotocine," by Freidinger, J. Org. Chem., 43:4800–4803 (1978).
K.—E. Andersson, B. Bengtsson and O. Paulsen, Desamino–8–D–Argomome Vasopressin (DDAVP): Pharmacology and Clinical Use 1988; 24(7): 509–528.

*Primary Examiner*—Jill Warden
*Assistant Examiner*—Sheela J. Huff
*Attorney, Agent, or Firm*—Hopgood, Calimafde, Kalil & Judlowe

[57] ABSTRACT

A process for the manufacture of 1-deamino-8-D-arginine vasopressin (DDAVP) comprising, condensing a preparation of Mpa($R^1$)-Tyr-Phe-Gln-Asn-Cys($R^2$)-Pro-OH (SEQ ID NO: 1), where $R^1$ and $R^2$ are sulfhydryl-protecting groups, with the dipeptide ($R^3$)-D-Arg(HCl)-Gly-NH$_2$, where $R^3$ is an acid-sensitive amino-protecting group, to form Mpa($R^1$)-Tyr-Phe-Gln-Asn-Cys($R^2$)-Pro-D-Arg(HCl)-Gly-NH$_2$ (SEQ ID NO: 1), which is oxidized with iodine in a protic solvent. The reaction mixture containing the oxidized product can be purified by ion exchange chromatography on a cation exchange resin equilibrated with acid. Also disclosed is high-purity DDAVP obtained by this process and its use for treating diurea.

15 Claims, No Drawings

PROCESS FOR MANUFACTURE OF 1-DEAMINO-8-D-ARGININE VASOPRESSIN

FIELD OF THE INVENTION

The present invention relates to a new process for manufacture of high purity 1-deamino-8-D-arginine vasopressin for use in treating diurea. The method includes condensing Mpa($R^1$)-Tyr-Phe-Gln-Asn-Cys($R^2$)-Pro-OH (SEQ ID NO: 1) with ($R^3$)-D-Arg(HCl)-Gly-$NH_2$ and oxidizing the resulting peptide.

BACKGROUND

The hormone analog 1-deamino-8-D-arginine vasopressin (1-β-mercaptopropionic acid, 8-D-arginine)-vasopressin or desmopressin, hereinafter also abbreviated as "DDAVP", is an important antidiuretic for treatment of diurea, such as associated with diabetes insipidus, nocturnal enuresis, and urine incontinence.

While differing from native neurohypophyseal vasopressin by exchange of the terminal cysteine moiety by 1-β-mercaptopropionic acid, and replacement of arginine with D-arginine, 1-deamino-8-D-arginine vasopressin will, in the present specification, nevertheless be termed a "nonapeptide derivative." Similarly, synthetic starting materials and intermediates will be termed n-peptide derivatives, where n equals the total number of amino acid and pseudoamino acid moieties in the respective peptide.

The synthesis of DDAVP by homogeneous phase (U.S. Pat. No. 3,497,491 to Zaoral et al.) and by solid phase (Krchnak, V. and Zaoral M., 1979, Coll. Czechoslov. Chem. Commun. 44:1173– 1178) methods has been described. However, 1-deamino-8-D-arginine vasopressin is only obtained in amorphous form with currently known methodology and is, thus, difficult to purify. For therapeutic application, impurities such as those with pressor activity cause complications.

It is known in the art that yield can be increased at the sacrifice of purity, and vice versa, and that the larger the product molecule, the harder and more expensive it is to purify. The medical field demands high purity as a premium, thus, the prevailing emphasis has been on purity. However, currently known methods require excessive purification steps with the inevitable reduction in yield. Purification is costly in terms of manpower hours and the obvious loss of profits from reduced product yield.

Thus, there is a need in the art for synthetic routes for producing DDAVP, wherein the yield achieved in the final steps of synthesis is increased. This will reduce the need for extensive purification of intermediates and product, and provide a superior product in improved yield. There is also a need in the art for an improved method for DDAVP production which is relatively less complex and wherein impurities with pressor effect or other unwanted biological effects will be formed to a lessor extent or more easily eliminated in purification steps.

OBJECTS OF THE PRESENT INVENTION

Accordingly, it is an object of the present invention to provide a new process for the high yield manufacture of high purity 1-deamino-8-D-arginine vasopressin, DDAVP.

Another object is to provide a simple, economical process which produces high yields of high purity DDAVP by avoiding in its final steps complex, expensive purification processes.

SUMMARY OF THE INVENTION

The present invention is a process for the manufacture of 1-deamino-8-D-arginine vasopressin (I) comprising the steps of:

a)—preparing the heptapeptide: Mpa($R^1$)-Tyr-Phe-Gln-Asn-Cys($R^2$)-Pro-OH (II) (SEQ ID NO: 1), where $R^1$ and $R^2$ are sulfhydryl-protecting groups and are identical or different;

b)—condensing said heptapeptide with the dipeptide: ($R^3$)-D-Arg(HCl)-Gly-$NH_2$ (III), where $R^3$ is an acid-sensitive, amino-protecting group;

c)—forming the nonapeptide: Mpa($R^1$)-Tyr-Phe-Gln-Asn-Cys($R^2$)-Pro-D-Arg(HCl)-Gly-$NH_2$ (IV) (SEQ ID NO: 1); and d)—oxidizing the nonapeptide (IV) with iodine in a protic solvent or solvent mixture.

The preferred method of preparing the heptapeptide (II) in step (a) is by:

condensation of the tripeptide: Mpa($R^1$)-Tyr-Phe-X (V), where X is a reactive moiety taking the place of the hydroxyl group, —OH, in the carboxylic group of Phe, with the tetrapeptide: $R^3$-Gln-Asn-Cys($R^2$)-Pro-OH (VI).

The sulfhydryl-protecting radicals $R^1$ and $R^2$ can be identical or can be, independent of the other, acetamidomethyl (Acm), tert-butyl, tert-butylsulfenyl, p-methylbenzyl, p-methoxybenzyl, 2-(3-nitropyridine sulfenyl), ethylcarbamoyl, triphenylmethyl, or 9-fluorenylmethyl.

According to a preferred embodiment of the invention, the sulfhydryl-protecting groups $R^1$ and $R^2$ are both acetamidomethyl. According to another preferred embodiment of the invention the amino-protecting group $R^3$ is N-tert-butyloxy (Boc).

It is furthermore preferred for the reactive moiety X to be an activated carboxylic acid ester, such as an ester of p-nitrophenol or hydroxysuccinimide, or a non-activated carboxylic acid ester, such as a methyl, ethyl or benzyl ester, or an azide. Thus, the reactive moiety X can be an alkoxy, aryloxy or azido, with the alkoxy preferably being a succinimidoxy and the aryloxy preferably being p-nitrophenyloxy.

In the above-described method, the oxidation with $I_2$ of step (d) is carried out at pH below 5.0, preferably between pH 1.5–4.3.

The present method allows purification of the reaction mixture essentially as obtained from the oxidation with iodine in step (d) after all synthesis is complete without interruption. A preferred purification route is via ion exchange chromatography on a cation exchange resin equilibrated with acid. It is also preferred for the ion exchange resin used for purification to contain sulfonate groups. The purification can be further refined such as with an additional gel chromatography step.

According to the present invention, there is also disclosed high-purity DDAVP prepared according to the inventive processes and its use in treating diurea caused by such ailments as diabetes insipidus, nocturnal enuresis, and urinary incontinence.

DETAILED DESCRIPTION

The present invention will now be explained in more detail by reference to a preferred, non-limiting embodiment, in which $R^1$ and $R^2$ are both acetamidomethyl, $R^3$ is N-tert-butyloxy and X is —$NHNH_2$.

EXAMPLE 1

Boc-Gln-Asn-Cys(Acm)-Pro-OH (X)

BocCys(Acm)ONp is prepared from BocCys(Acm)OH (Novabiochem, Läufelingen, CH) and p-nitrophenol by reaction with N,N'-dicyclohexylcarbodiimide (DCC) in etyl acetate and used without purification for the preparation of Boc-Cys(Acm)-Pro-OH (XII) by reacting it with H-Pro-OH in DMF/etyl acetate/H$_2$O at 0° C. while keeping pH neutral by addition of Et$_3$N. Yield 81%. Purity>95% (TLC).

Boc-Asn-Cys(Acm)-Pro-OH (XIII) is obtained by deblocking XII in HCl/HOAc att room temperature, dissolving the thus obtained raw H-Cys(Acm)-Pro-OH.HCl in DMF and neutralizing it with Et$_3$N, and adding Boc-Asn-ONp (Novabiochem, Läufelingen, CH) at −5° C. while keeping pH neutral. XIII is isolated in 81% yield. $[\alpha]_D^{20}$= −77.1° (1 g/100 ml DMF). The tetrapeptide derivative X is prepared from XIII and Boc-Gln-ONp (Novabiochem, Läufelingen, CH) in a way corresponding to the preparation of XIII from XII and Boc-Asn-ONp. Yield 78.5%; $[\alpha]_D^{20}$= −89.7° (1 g/100 ml H$_2$O).

EXAMPLE 2

Mpa(Acm)-Tyr-Phe-NHNH$_2$ (XI)

Mpa(Acm)-Tyr-OEt (XIV) is prepared by reacting H-Tyr-OEt.HCl with Mpa(Acm)-OH (Bachem AG, CH) and DCC in DMF containing 1-hydroxybenzotriazole (HOBt) at 0° while maintaining pH at 7 (Et$_3$N). Yield 48%. The hydrazide XI is prepared by reacting the ester XIV with H-Phe-N$_2$H$_3$ in DMF/H$_2$O under catalysis by α-chymotrypsin. Yield 90%; m.p. 240°–242° C.

EXAMPLE 3

Mpa(Acm)-Tyr-Phe-Gln-Asn-Cys(Acm)-Pro-OH (VII)

(SEQ ID NO: 1)

Boc-Gln-Asn-Cys(Acm)-Pro-OH (X) (11.7 g) is dissolved in 56 ml trifluoroacetic acid (TFA) which is evaporated after being kept for one hour at room temperature. The residue is dissolved in 19 ml dimethyl formamide (DMF) and cooled, and pH is adjusted to 7 (Et$_3$N). Mpa(Acm)-Tyr-Phe-NHNH$_2$ (XI; 11.0 g) is dissolved in 115 ml DMF, the solution is cooled to −18° C., HCl/ethyl acetate (15.8 ml; 3,2M) is added and the solution is kept at −15° C. Isoamylnitrite (3.5 ml) is added and the solution is stirred at about −10° C. for 15 min. After cooling to −20° C. pH is adjusted to 7 (Et$_3$N).

The solution of the deblocked tetrapeptide in DMF is added and the mixture stirred at −5° C. After the reaction is virtually complete (99.5% conversion of the deblocked tetrapeptide as determined by TLC), precipitated salt is filtered off and the volume reduced to 60 ml by evaporation in vacuo. EtOH (99.5%; 215 ml) is added and the solution heated to 60° C. After cooling to ambient temperature pH is adjusted to 2.5 (conc. HCl). The precipitate is filtered off, washed with 99.5% EtOH, and dried to yield 17.6 g of white crystals; yield 85%, mp. 188°–191° C.

EXAMPLE 4

Boc-D-Arg(HCl)-Gly-NH$_2$ (VIII)

H-Gly-NH$_2$.HCl (2.6 g) and 1-hydroxy-benzotriazole (HOBt; 3.3 g) is suspended in 34 ml DMF and the solution is cooled to −10° C. Et$_3$N (2.0 ml) is added and the mixture stirred for 15 min. Boc-D-arginine(HCl) (6.8 g) is added and the temperature brought to 0° C. DCC (4.5 g) dissolved in 4.5 ml DMF is added and pH adjusted to 6.0 (Et$_3$N). After complete conversion, the formed precipitate is removed by filtration and the filtrate evaporated in vacuo.

The residue is dissolved in 80 ml water, the solution is cooled to 0° C. and pH adjusted to 3 (1M HCl). After removing HOBt by filtration the solution is extracted with dichloromethane. The aqueous phase is reduced to a volume of 20 ml in vacuo, subjected to azeotropic distillation with butanol (4 x), and its volume brought to 68 ml by addition of BuOH. The solution is extracted with 0.1M HCl containing 10% NaCl (w/w) and 5% butanol (v/v), and thereafter reduced to half its volume by distillation.

After repeating the azeotropic distillation with butanol and removing NaCl by filtration, the solution is poured into an eightfold excess (v/v) of isopropyl acetate, and the precipitate is collected by filtration and washed with isopropyl acetate. Compound VIII was obtained in form of a white amorphous powder; yield 6.8 g (90%), $[\alpha]_D^{20}$=4.3°.

EXAMPLE 5

Mpa(Acm)-Tyr-Phe-Gln-Asn-Cys(Acm)-Pro-D-Arg (HCl)-Gly-NH$_2$ (IX)

(SEQ ID NO: 1)

BOC-D-Arg(HCl)-Gly-NH$_2$ (VIII) (6.8 g) is dissolved in 23 ml acetic acid and 20 ml HCl/HOAc (2.2M) is added. After stirring for 1.5 h at room temperature, the solution is evaporated under reduced pressure and the residue dissolved in 30 ml DMF. The deblocked dipeptide is precipitated in form of oily droplets by adding xylene (31 ml). After decantation of the supernatant, the residue is washed with xylene and remaining solvent removed in vacuo. The residue is dissolved in 110 ml DMF and the solution cooled to −10° C. By addition of Et$_3$N pH is adjusted to 7.5.

Mpa(Acm)-Tyr-Phe-Gln-Asn-Cys(Acm)-Pro-OH (VII) (SEQ ID NO: 1) (14 g) and 2.1 g HOBt are dissolved in 65 ml DMF and the deblocked dipeptide H-D-Arg(HCl)-Gly-NH$_2$ in DMF obtained in the preceding step and the calculated amount of DCC is added. After 90% conversion (TLC) DCU is filtered off and and the solution reduced to a volume of 100 ml, heated to 60° C. and poured into 310 ml EtOH/EtOAc 85:15 (v/v).

The precipitate is collected by filtration and washed with EtOH/EtOAc 85:15. Compound IX was obtained in form of a white powder (yield 15.5 g (84.9%), m.p. 182°–185° C.) with a purity of 94.5% (HPLC).

EXAMPLE 6

1-DEAMINO-8-D-ARGININE VASOPRESSIN (SEQ ID NO: 2)

Mpa—Tyr—Phe—Gln—Asn—Cys—Pro—D—Arg—Gly—NH$_2$ (I)

(acetate)

10 g of Mpa(Acm)-Tyr-Phe-Gln-Asn-Cys(Acm)-Pro-D-Arg(HCl)-Gly-NH$_2$ (IX) (SEQ ID NO:1) is dissolved in 10 l acetic acid/water 1:9 (v/v). The blocked nonapeptide derivative IX is oxidized at room temperature by addition of 2 g iodine dissolved in 80 ml ethanol by means of a roller pump, the feeding speed of which is controlled by a UV-monitor in order to keep the amount of free iodine in the reaction medium low. Conversion of IX is monitored by high-speed HPLC. A yellow colour persists after the entire amount of IX has been consumed.

The solution from the reaction containing the products is passed through a short glass column containing 1.6 l S-Sepharose® FF (Pharmacia, Sweden) equilibrated with aqueous acetic acid. 1-deamino-8-D-arginine vasopressin (I) is eluted with 0,08 M NH$_4$Ac/AcOH buffer (24 l, pH 4.1; fractions monitored by HPLC analysis). Fractions containing DDAVP (I) in purity>99 % (disregarding from buffer components) are combined. The solution containing the acetate of pure title compound is concentrated by partial evaporation of solvent in vacuo or by reverse osmosis, and finally freeze dried. White fluffy powder.

DDAVP (I) is further purified by gel filtration on Sephadex G25 (0.1M acetic acid). Elution is followed by analyzing individual fractions with HPLC. The combined fractions containing pure product are combined and freeze dried. DDAVP (I) in a purity >99% is obtained in form of its diacetate in a yield of about 5 g. White fluffy powder. Yield 53%.

EXAMPLE 7

Comparison tests were performed with the DDAVP made according to Examples 1–6 with 1-deamino-8-D-arginine vasopressin made with a known homogeneous phase process.

The overall yield of DDAVP synthesized according to the homogeneous phase method disclosed in U.S. Pat. No. 3,497,491 (starting from β-mercaptopropionic acid) is 5.0%. The corresponding overall yield for 1-deamino-8-D-arginine vasopressin (I) prepared by the process according to the present invention [including preparation of Mpa(Acm)-OH] is 7.0%, an improvement by 40%. The process according to the present invention, with the synthethic route starting from β-mercaptopropionic acid [including preparation of Boc-Cys(Acm)-OH] produced overall yield of 1-deamino-8-D-arginine vasopressin (I) of 10.7%.

Even more important is the high yield obtained in the last three steps of the process according to the present invention, that is, 38% for compound X and 45% for compound VIII. Yields for the last three steps of known processes are typically in the range of about 8.5%–17% or about 10–20%. In terms of process economy, product losses in final stages are more costly than in initial stages, and the present method is, thus, much more cost effective.

The process according to the present invention not only provides DDAVP in substantially better yield than the known homogeneous phase processes, but does so also in substantially higher purity.

Precise information about purity of end product is lacking in U.S. Pat. No. 3,497,491, no content of pure DDAVP for the end product being provided, and the results of elemental and amino acid analysis given are only useful for structural confirmation. Furthermore, while optical rotation, in principle, can be measured with great precision, the values described therein of $-65°\pm2°$ for $[\alpha]_D^{25}$ is not useful.

However, information about pressor effect in the table in column 3 of U.S. Pat. No. 3,497,491 may be used for assessment of purity. 1-deamino-8-D-arginine vasopressin (I) prepared according to U.S. Pat. No. 3,497,491 is described as having measurable pressor side-effects. Later studies have demonstrated that 1-deamino- 8-D-arginine vasopressin (I), in fact, does not possess such pressor activity if meticulously purified. Such further purification, however, can be only done at the sacrifice of yield if done following the methods currently known.

The pressor side-effects caused by impurities contained in products prepared according to known methods include pharmacological complications such as vascular hypertension. Thus, "purity" encompasses two aspects, first the degree of actual, active DDAVP content in the end product and second, the absence of medically harmful impurities. The 1-deamino-8-D-arginine vasopressin (I) made according to the present method is virtually free from such potentially harmful impurities.

While the invention has been fully described herein, one skilled in the art could modify the various steps in the process, the reagents used and the various reaction conditions and achieve similar results. Such modifications are encompassed within the scope and spirit of the present disclosure.

What is claimed is:

1. A method for synthesis of 1-deamino-8-D-arginine vasopressin, comprising the steps of:
    a) preparing the heptapeptide: Mpa($R^1$)-Tyr-Phe-Gln-Asn-Cys($R^2$)-Pro-OH (SEQ ID NO:1), where $R^1$ and $R^2$ are sulfhydryl-protecting groups;
    b) condensing the heptapeptide from step (a) with the dipeptide: ($R^3$)-D-Arg(HCl)-Gly-NH$_2$, where $R^3$ is an acid-sensitive, amino-protecting group;
    c) forming the nonapeptide: Mpa($R^1$)-Tyr-Phe-Gln-Asn-Cys($R^2$)-Pro-D-Arg(HCl)-Gly-NH$_2$ (SEQ ID NO: 1); and
    d) oxidizing the nonapeptide from step (c) with iodine in a protic solvent.

2. The method of claim 1, wherein said sulfhydryl-protecting radicals $R^1$ and $R^2$ can be identical or can be, independent of the other, selected from the group consisting of acetamidomethyl, tert-butyl, tert-butylsulfenyl, p-methylbenzyl, p-methoxybenzyl, 2-(3-nitropyridine sulfenyl), ethylcarbamoyl, triphenylmethyl, and 9-fluorenylmethyl.

3. The method of claim 2, wherein said sulfhydryl-protecting radicals $R^1$ and $R^2$ are both acetamidomethyl.

4. The method of claim 1, wherein said amino-protecting group $R^3$ is N-tert-butyloxy.

5. The method of claim 1, wherein said heptapeptide of step (a) is prepared with a process, comprising:
    condensing the tripeptide: Mpa($R^1$)-Tyr-Phe-X, where X is a reactive moiety taking the place of the —OH, in the —COOH of Phe, with the tetrapeptide: $R^3$-Gln-Asn-Cys($R^2$)-Pro-OH.

6. The method according to claim 5, wherein said reactive moiety X is selected from the group consisting of alkoxy, aryloxy and azido.

7. The method according to claim 6, wherein the alkoxy is succinimidoxy.

8. The method according to claim 6, wherein the aryloxy is p-nitrophenyloxy.

9. The method according to claim 1, wherein said oxidation with iodine of step (d) is carried out at pH below 5.0.

10. The method according to claim 9, wherein said oxidation with iodine is carried out at a pH between 1.5–4.3.

11. The method according to claim 1, wherein the reaction mixture containing said oxidized nonapeptide from step (d) is purified by ion exchange chromatography on a cation exchange resin equilibrated with an acid.

12. A method for treating diurea in humans comprising the administration of a therapeutic amount of said 1-deamino-8-D-arginine vasopressin (DDAVP) prepared according to the method of claim 1.

13. A compound prepared according to the method of claim 1 containing the following structure:

(SEQ ID NO: 2)

Mpa—Tyr—Phe—Gln—Asn—Cys—Pro—D—Arg—Gly—NH$_2$
|_____|

---

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:1:

Tyr  Phe  Gln  Asn  Cys
        1                        5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:2:

Tyr  Phe  Gln  Asn  Cys  Pro
        1                        5

14. A therapeutic for treating diurea in humans comprising the compound according to claim 13.

15. A method for treating diurea in humans comprising the administration of a therapeutic amount of the compound according to claim 13.

\* \* \* \* \*